United States Patent [19]

Nieh

[11] Patent Number: 5,068,456
[45] Date of Patent: Nov. 26, 1991

[54] PREPARATION OF NONIONIC SURFACTANTS BY OXYALKYLATION WITH A PHENOLIC ACTIVATED MAGNESIUM CATALYST

[75] Inventor: Edward C. Y. Nieh, Austin, Tex.

[73] Assignee: Texaco Chemical Company, White Plains, N.Y.

[21] Appl. No.: 615,114

[22] Filed: Nov. 19, 1990

Related U.S. Application Data

[63] Continuation-in-part of Ser. No. 466,098, Jan. 16, 1990, abandoned, which is a continuation of Ser. No. 205,753, Jun. 13, 1988, abandoned.

[51] Int. Cl.$^5$ .............................................. C07L 41/03
[52] U.S. Cl. ..................................... 568/618; 518/620
[58] Field of Search ................................. 568/618, 620

[56] References Cited

U.S. PATENT DOCUMENTS 4,453,022 6/1984 McCain et al. .
4,453,023 6/1984 McCain et al. .
4,465,877 8/1984 Edwards .

FOREIGN PATENT DOCUMENTS 1185992 4/1985 Canada .

Primary Examiner—Howard T. Mars
Attorney, Agent, or Firm—Jack H. Park; Kenneth R. Priem

[57] ABSTRACT

Nonionic surfactants containing a narrow molecular weight distribution is obtained by the use of a magnesium-containing catalyst which comprises reacting a reactive hydrogen compound selected from the group consisting of monohydric alcohols having from about 6 to 30 carbon atoms with an alkylene oxide having from 2–4 carbon atoms at a temperature at which the reaction proceeds in the presence of at least a catalytic amount of a phenolic activated magnesium catalyst containing phosphorus.

4 Claims, No Drawings

PREPARATION OF NONIONIC SURFACTANTS BY OXYALKYLATION WITH A PHENOLIC ACTIVATED MAGNESIUM CATALYST

CROSS-REFERENCE

This application is a continuation in part of Ser. No. 07/466,098 filed Jan. 16, 1990, now abandoned, which is a continuation of Ser. No. 07/205,753 filed Jun. 13, 1988, now abandoned.

This application is related to application Ser. No. 07/205,754 now U.S. Pat. No. 4,892,977.

BACKGROUND OF THE INVENTION

The present invention relates to a process for preparation of nonionic surfactants wherein the molecular weight distribution of the nonionic surfactants obtained is in a narrow range.

The instant invention relates to the preparation of improved nonionic surfactant active agents and more particularly, to a process for the oxyalkylation of certain reactive hydrogen compounds to prepare nonionic surfactant active agents wherein the molecular weight distribution is narrow and wherein a novel phenolic activated magnesium-containing catalyst is employed to produce the nonionic surfactants.

Low molecular weight condensation products of an alkylene oxide, particularly ethylene oxide, or mixtures of alkylene oxides such as ethylene and propylene oxide with an alcohol are well known and for a long time have been prepared commercially for use in detergents, cleansing agents, dry cleaning materials, wetting and emulsifying agents and the like. These products are conventionally produced by reacting the reactive hydrogen compound with the alkylene oxide in the presence of a strongly alkaline or an acidic catalyst. Such preparative procedures result in the production of a mixture of relatively low molecular weight (up to about 2000) condensation product species containing a number of alcohol derivatives having different molecular proportions of alkoxylate. Thus, the reaction products generally obtained are, in reality, a mixture of derivatives of the alcohol moiety containing different molecular proportions of alkylene oxide units, i.e., having varying molar rations of alcohol to alkylene oxide, and a wide range of molecular weights as well as having a certain proportion of unreacted alcohol. Moreover, as is well known, the conventional designation of the number of alkylene oxide units present per molecule of an alcohol alkoxylate is a designation of the average number of alkylene oxide units per molecule and that a substantial proportion of the alcohol alkyoxylates present are present as alcohol alkyoxylates having a greater and a lesser number of alkylene oxide units present than the actual average value would indicate. Such designations of such products is well understood in the art and will be employed herein consistent with its well understood meaning.

It is generally desirable to restrict, i.e. control the breath of the molecular weight distribution of the mixture to adjacent analogues of the desired product insofar as possible, since, as is well known, the number of moles of alkylene oxide in the reaction product is a major factor in determining what the properties of such products are, but as a matter of course it is quite difficult to control the molecular weight distribution. Acidic catalysts tend to give a narrower molecular distribution than alkaline catalysts, but, unfortunately, also contribute to the formation of undesired by-products. Thus, alkaline catalysts which are typically a strong base such as alkali metal hydroxides and alcoholates are generally used as the more efficient type of oxyalkylation catalyst, but the molecular distribution of the products are more diffuse, containing a greater proportion of lower and higher molecular weight species and smaller amounts of the species with the desired number of moles of alkylene oxide per mole of alcohol. For example, an 8-mole ethylene oxide (EO) adduct per mole of 1-dodecanol will contain not only the 8-mole EO adduct specie but also lower mole adducts and higher mole adducts. Lower mole adducts in the product mixture will range down to the one-mole adduct and higher adducts will extend up to 14 or 15 and beyond. The molecular weight distribution is a measure of the relative amounts of the various adducts in the product mixture and can be represented in the form of a generally bell-shaped curve where the amount of each adduct species is plotted versus the number of moles of epoxide in the specie or of a description of the relative amount of each individual adduct. When the molecular weight distribution is characterized by a bell-shaped curve, a narrower distribution gives a sharper curve which is, higher at the middle and lower at the ends. A broader distribution curve would be lower at the middle portion of the range and higher at the ends, and such is not desirable.

Heretofore, several methods have been suggested for providing reaction products of an active hydrogen compound, e.g., alcohol, and epoxides which have a narrower range of molecular weights and molecular distribution of the epoxide units, and/or which reduce or eliminate the production of undesirable poly-(alkylene glycol) and cyclic and straight chain ether by-products. For example, in U.S. Pat. No. 4,112,231 to Weibull et al it is disclosed that the use of certain neutral inorganic fluoborate and perchlorate salts will catalyze the reaction of epoxides with active hydrogen compounds to give products having a relatively narrower molecular distribution, i.e., a more limited range of molecular species and a larger proportion of desired molecular species; in U.S. Pat. No. 3,682,849 to Smith et al improved ethoxylated derivatives in $C_{11}$–$C_{18}$ alcohols are prepared by removing unreacted alcohol and lower ethoxylates from the ethoxylate mixture prepared by convention methods by use of vapor phase separation techniques; in U.S. Pat. No. 2,870,220 to Carter, a two-stage process is disclosed for preparing monoalkyl ethers of ethylene glycol and polyethylene glycols of more restricted molecular weight range wherein an alkanol and ethylene oxide is reacted in the presence of an acidic catalyst during the first stage and then in the second-stage after removal of acid catalyst and unreacted alkanol, reacting the mixture with ethylene oxide in the presence of an alkali metal alcoholate of the initial alkanol; and in the U.S. Pat. No. 3,972,948 to Laemmle et al there is disclosed a method of preparing mono- and poly-glycol ethers substantially free of undesired alkylene glycol by-products which method involves heating a reaction mixture containing an alkylene oxide and an alcohol in the presence of a catalyst containing alkali or alkaline earth cations wherein some or all of the catalyst is an anhydrous high boiling liquid residue prepared by concentrating the liquid residue from the same or different etherification processes after removal of the glycol ether product from the reaction mixture. None of the above-described processes and special catalysts disclosed in the art, however, are completely satisfactory in preparing a product with a desired molecular distribution in that such generally require multi-stage procedures or special acid-resistant equipment, may form undesirable by-products or simply do not provide sufficient control over the molecular weight distribution to be of a satisfactory nature. Thus, it would be highly desirable to develop a process where in the reaction of an alkylene oxide (epoxide) with an alcohol could be more readily carried out to prepare surfactant products that have a relatively narrower molecular weight distribution of analogue species and contain only small amounts, at most, of undesirable poly(alkylene glycol) and ether by-products.

Several patents are concerned with the preparation and advantages of nonionic surfactant products having a narrower molecular weight distribution. For example, U.S. Pat. No. 4,239,917 to Yang discloses the use of a class of basic barium materials as catalysts in the preparation of reaction products of alcohols and ethylene oxide so as to provide a product with a narrow, high mole adduct distribution while providing relatively low levels of undesirable by-products and unreacted free alcohol. The molecular weight distribution factor of the products produced during the oxyalkylation reaction is discussed at length by patentee and the differences in the molecular weight distribution of reaction products prepared with conventional alkali metal catalysts such as sodium hydroxide and those prepared using a barium catalyst of the invention is shown by graphical representations. The patent, to Yang, also shows that other alkaline earth metal materials, such as calcium hydroxide, magnesium oxide, and strontium hydroxide, were ineffective as catalysts for the oxyalkylation reaction. Thus, patentee demonstrates that significant differences exist in catalytic effectiveness even between the various alkaline earth metals and not only between the barium catalysts of the invention and alkali metal hydroxides.

Further, U.S. Pat. Nos. 4,210,764 and 4,223,164 to Yang et al are concerned with the problem of the molecular weight distribution of products prepared by oxyalkylation of alcohols using conventional alkaline catalysts and are directed to overcoming an induction period problem frequently observed when employing barium-containing catalysts, such as those disclosed in U.S. Pat. No. 4,239,917. The patentees suggest he use of various phenols for use as a promoter for the barium-containing catalyst to overcome the induction period difficulty, and U.S. Pat. No. 4,223,164 disclose that with such promoters certain basic strontium materials may also be employed as a catalyst for the oxyalkylation reaction.

U.S. Pat. No. 4,453,022 describes the process for preparing nonionic surfactants containing a narrow molecular weight distribution by the use of a catalytic amount of a basic salt of calcium and/or strontium selected from the group consisting of hydroxide, alkoxide and phenoxide and a catalytic amount of an oxyalkylation catalyst promoter.

U.S. Pat. No. 4,721,817 describes alkylene oxide adducts of higher alkanols characterized by relatively narrow range distribution of alkylene oxide adducts by the use of a catalytically effective amount of a catalyst which combines one or more phosphorus-containing acids with one or more aluminum compounds selected from the group consisting of aluminum alcoholates and aluminum phenolates.

European Patent App. 0,082,569 shows alkanol soluble basic compounds of magnesium (which could include magnesium alkoxide) activated by alcohol ethoxylate.

It is believed that the instant invention provides an improved method for making narrow range oxyalkylation products using a novel phenolic activated catalyst containing magnesium.

SUMMARY OF THE INVENTION

In accordance with the present invention, there is provided a process and a catalyst for carrying out the process for the preparation of nonionic surfactants having a molecular weight distribution which is narrow. The process comprises reacting a reactive hydrogen compound selected from the group consisting of monohydric primary alcohols having between 6 and 30 carbon atoms, both branched and linear, with an alkylene oxide having 2–4 carbon atoms at a temperature at which the reaction proceeds in the presence of at least a catalytic amount of catalyst that is produced from the reaction of magnesium and a phenolic compound resulting in a magnesium phenoxide. Alternatively, a magnesium alkoxide of the alkanol may be generated in situ, for example, from the reaction of magnesium and a mixture of high molecular weight alcohol(s) and low molecular weight alcohol(s) and the subsequent removal of the low molecular weight alcohols or simply by mixing a high molecular weight alkanol with magnesium and low molecular weight alcohol(s) and the subsequent removal of the low molecular weight alcohol(s). The resulting magnesium-containing compound may then be reacted, with a phenolic compound to product the catalyst of the invention.

DESCRIPTION OF THE PREFERRED EMBODIMENTS

The process of the invention comprises reacting a reactive hydrogen compound selected from the group consisting of monohydric primary alcohols having between 6 and 30 carbon atoms, more preferably between about 10 and 24 carbon atoms and especially preferably liner alkyl primary alcohols comprising from about 6–30 carbon atoms or their mixture with an alkylene oxide having 2–4 carbon atoms in the presence of an oxyalkylation catalyst comprising a catalytically effective amount of a catalyst that is produced as described in the summary.

The reaction may be conducted in a conventional manner, that is, the reactive hydrogen compound and the oxyalkylation catalyst are placed in a reactor, the selected alkylene oxide is added to the reaction mixture until the desired number of moles have been reacted with the reactive hydrogen compound and the product is removed from the reactor and neutralized. The reaction may be, conducted in the presence of a solvent, but usually a solvent is not necessary. The process may be batch or continuous.

The temperature at which the reaction proceeds is not especially critical and generally depends upon the desired rate of reaction and sound engineering practices. However, a temperature between about 80° C. and about 260° C. is usually acceptable with a temperature between about 120 and about 200 being preferred. The pressure likewise of the reaction is not especially critical, however, the use of ethylene oxide and/or propylene oxide as the alkylene oxide usually requires a pressurized reactor. In general the pressure may range between about 20 psig and 200 psig.

The reaction product may be neutralized and catalyst residue be removed with any conventional technique known to those skilled in the art.

Alcohols which are suitable for the practice of the invention as the reactive hydrogen compound are monohydric primary alcohols and alkyl phenol having between about 6 and about 30 carbon atoms and especially found useful are linear and branched alkyl primary alcohols of about 8–24 carbon atoms.

Alcohols which are suitable for use in the practice of the invention as the reactive hydrogen compound are primary and secondary aliphatic alcohols which are straight or branched chain and have between about four and about twenty-five carbon atoms. Exemplary of such alcohols are those derived by hydrogenation of natural fats and oils, such as CO and TA alcohols, trademark of and sold by Proctor and Gamble Co., such as CO-1214N alcohol, CO-1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be alkoxylated. Examples of these alcohols are ALFOL alcohols, trademarks of and sold by Continental Oil Co., such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Co., such as NEODOL 23 alcohol, NEODOL 25 alcohol, NEODOL 1418 alcohol; TERGITOL-L, trademark of Union Carbide Corp., such as TERGITOL-125 alcohol; LIAL alcohols, trademark of and sold by Liquichimica Co. such as LIAL 125; and isodecyl and tridecyl alcohols, sold by Exxon Corp., such as isodecyl alcohol and tridecyl alcohol, Guebet alcohols can also be ethoxylated. Representative examples of these alcohols are STAN-DAMUL alcohols, trademark of and sold by Henkel Chemical Co., such as STANDMUL GT-12 alcohol, STADMUL GT-16 alcohol, STANDMUL GT-20 alcohols, STANDMUL GT-1620 alcohol. Secondary alcohols can also be used, such as TERGITOL 15 alcohol, trademark of and sold by Union Carbide Corp.

Generally, usable alcohols include 1-decanol; 1-undecanol; 1-dodecanol; 1-tricecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol;2-pentyl-1-nonanol;2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; tetradecanol; 7-tetradecanol; 2-hexadecanol; 3-hexadecanol; 5-hexadecanol; 6-hexadecanol; 7-hexadecanol; 8-hexadecanol; 2-octadecanol; 3-octadecanol; 3-octadecanol; 4-octadecanol; 5-octadecanol; 6-octadecanol; 7-octadecanol; 8-octadecanol; 9-octadecanol; 9-octadecanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-; undecanol;3-hexyl-1-hexyl-1-undecanol;3-hexyltridecanol;3-octyl-1-tridecanol;2-methyl-2-undecanol;3-methyl-3-undecanol;4-methyl-4-undecanol; 2-methyl-2-tridecanol; 3-methyl-3-tridecanol; 4-methyl-3-tridecanol; 4-methyl-4-tridecanol; 3-ethyl 3-decanol; 3-ethyl-3-dodecanol; 2,4,6,8-tetramethyl-2-nonanol; 2-methyl-3-undecanol; 2-methyl-4-undecanol 4-methyl-2-undecanol; 5-methyl-2-undecanol; 4-ethyl-2-decanol; 4-ethyl-3-decanol.

Also employable as the reactive hydrogen compound are the difunctional propylene oxide polymers having a molecular weight of 1000 to 5000, and preferably 1700 to 4100 made with the same catalyst as disclosed herein. The propylene oxide polymers having a molecular weight of 1000 to 5000 contain from 17 to 86 oxypropylene units in the molecular. These compounds are well known, being generally obtained by polymerization of propylene oxide or by the addition of propylene oxide to lower molecular compounds with 2 to 6 carbon atoms containing at least 2 reactive hydrogen atoms.

Alkylene oxides which may be employed in accordance with the invention include those alkylene oxides having between about 2 and about 4 carbon atoms and include, for example, ethylene oxide, 1,2-propylene oxide, and butylene oxides such as 1,2-butylene oxide, and mixtures thereof. The number of moles of alkylene oxides employed according to the present invention may vary widely depending on the reactive hydrogen compound o be adducted and the particular application for which the surface active agent is to be employed. In general, between 2 and about 80 or greater moles of alkylene oxide per mole of reactive hydrogen compound may be employed with greater molar ratios being employed if higher molecular weight products are desired. Insofar as propylene oxide and/or butylene oxide are used in combination with ethylene oxide, the molar ratio of ethylene oxide to propylene oxide—or butylene oxide may be between about 100:1 and about 3:1, preferably between 50:1 to 5:1.

In the process of this invention, the reaction of an alkylene oxide with a reactive hydrogen compound is carried out in the presence of an oxyalkylation catalyst comprising a product produced from the reaction of an alkaline magnesium compound and a phosphorus-containing acid or ester. More specifically, the alkaline magnesium component is the magnesium alkoxide of the alkanol or magnesium phenoxide. The alkaline magnesium component can be generated in situ by various means, for example, by mixing the high molecular weight alkanol with magnesium alkoxide of low molecular weight alcohols and the subsequent removal of the low molecular weight alcohol or by reacting magnesium halide with sodium alkoxide of the high molecular weight alcohol and the subsequent removal of sodium halide or reacting the high molecular weight alcohol with alkaline magnesium compounds such as diethyl magnesium, dicyclopentadienyl magnesium, magnesium ammoniate, magnesium amide and magnesium thiophenolate.

The phenolic compound is selected from phenol and alkyl substituted phenol, for example, preferred are nonylphenol, dodecylphenol and dinonylphenol.

The reaction scheme below shows a general method of making a catalyst suitable for this invention. The structures shown are believed to be accurate providing a stoichimetric quantity of ROH is available. If less than a stoichiometric quantity of ROH is present, then the catalyst exists in the form of a mixture of $Mg(OR)_2$, $Mg(OCH_3)_2$ AND $CH_3O-Mg-OR$. The scheme shown is for illustration of the method for preparing a catalyst of the invention.

Route 1

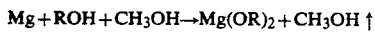

where ROH is a phenolic compound

Route 2

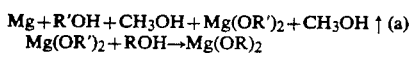

where

R' is $C_6$ to $C_{30}$ alkyl and R is phenolic

The above reaction schemes show the use of methanol. It is of course acceptable to use other low molecular weight alcohols such as ethanol and isopropanol, for example. The useful high molecular weight alcohols show as R'OH are the same as those described above as the reactive hydrogen compound.

The catalyst of the invention produces narrow range alkoxylates that contain less oil soluble oligomers and less water soluble oligomers thus enhancing their usefulness. The peak of molecular weight distribution is especially sharp using the process of this invention. As the data will show, this invention produces products containing less of the unreacted alcohol and 1 to 2 mole adducts of alkylene oxide that affect the performance of the product distribution.

EXAMPLE 1

Magnesium nonylphenoxide was prepared by reacting magnesium turnings (52 grams) with methanol (100 grams) in a three-liter three-neck flask fitted with stirrer, condenser, thermometer and nitrogen inlet. Magnesium turnings were added in 5-gram portions every 10 minutes and the exothermio reaction was controlled at 35° to 45° C. with the aid of an ice water bath. When all the magnesium was reacted, nonylphenol (880 grams) was added. The resulting solution contained 2.7% soluble magnesium according to atomic absorption analysis.

EXAMPLE 2

Magnesium methoxide was prepared by reacting magnesium turnings (60 grams) with anhydrous methanol (1000 grams) in a 2-liter three-neck flask fitted with stirrer, condenser, thermometer and nitrogen inlet. Magnesium turnings were added in 6-gram portions every ten to twelve minutes. Occasionally an ice water bath was used to control reaction temperature in the 35° to 45° C. range. Crystalline magnesium methoxide was obtained after the nearly clear super saturated magnesium methoxide solution in methanol was allowed to stand overnight. The solubility of magnesium methoxide in methanol was estimated to be 1000 ppm by atomic absorption analysis of he mother liquor. Crystalline magnesium methoxide was collected and dried in a vacuum oven at 50° C. and 20 mm Hg pressure for several hours.

EXAMPLE 3

The preferred magnesium alkoxide catalyst concentrate was prepared by reacting magnesium turnings (82 gram) with a mixture of anhydrous methanol (920 grams) and EPAL 1214 alcohol (1000 grams, a mixture of dodecanol and tetradecanol, average molecular weight 197, available from Ethyl Corp.) in a three-liter three-neck flask fitted with stirrer, condenser, thermometer, and nitrogen inlet. The magnesium turnings were added in small portions every 10 to 12 minute periods. Occasionally, an ice water bath was used to control reaction temperature at 35° to 45° C. When all the magnesium turnings were reacted, the magnesium alkoxide catalyst concentrate remained as a stable clear solution.

EXAMPLE 4

To a clean, dried one-gallon kettle was charged EPAL 1214 alcohol (1870 grams) and magnesium catalyst concentrate containing 11.4 gram-atom of Mg in methanol solution. Methanol was stripped from the mixture by heating to 80° C. and 20 mm Hg pressure. Then ethylene oxide was added at 165° C. and 80 psig until the desired degree of ethoxylation was reached. The product was neutralized with acetic acid (34 grams). Results were given in Table 1.

EXAMPLE 5

An ethoxylation reaction conducted in the same manner as described in Example 4, except that ethylene oxide was added at 150° C. and 50 psig pressure. Results were given in Table 1.

EXAMPLE 6

An ethoxylation reaction conducted in the same manner as described in Example 4, except that a catalyst concentrate containing 22.8 gram-atom of Mg doubling the quantity used in Example 4. Results are given in Table 1.

EXAMPLE 7

To a clean and dried one-gallon kettle was charged EPAL 1214 alcohol (1834 grams) and a magnesium catalyst concentrate made in the same manner as Example 1 containing 2.3 gram-atom Mg and 38.7 grams of nonylphenol in methanol. After stripped off methanol, at 80° C. and 20 mm Hg pressure, ethoxylation was conducted at 165° and 80 psi pressure. The product was neutralized acetic acid. Results are given in Table 1.

EXAMPLE 8

To a clean and dried one-gallon kettle was charged EPAL 1214 alcohol (1870 grams and a magnesium catalyst concentrate containing 3.06 gram-atom Mg made as in Example 3 and 19 grams of nonylphenol in methanol solution. After stripped off methanol at 80° C. and 20 mm Hg pressure, ethoxylation was conducted in a similar manner as in Example 8. The slow reaction was terminated after 5.3 hours. Results are given in Table 1.

EXAMPLE 9

To a clean and dried one-gallon kettle was charged EPAL 1214 alcohol (1870 grams) and a magnesium catalyst concentrate containing 11.4 Mg made as in Example 3 and 49.8 grams of nonylphenol in methanol solution. After stripped off methanol at 80° C. and 20 mm Hg pressure, ethoxylation was conducted at 165° C. and 80 psi. Results are given in Table 1.

EXAMPLE 10

6391-4

Example 9 was repeated and results are given in Table 1.

EXAMPLE 11

Example 9 was repeated using a catalyst concentrate containing 22.8 gram-atom of magnesium catalyst and nonylphenol (100 grams). Results are given in Table 1.

EXAMPLE 12

Example 9 was repeated using a catalyst concentrate containing 6.8 gram-atom of magnesium and 62.7 grams of nonylphenol. Results are given in Table 1.

EXAMPLE 13

Example 9 was repeated using a catalyst concentrate containing 4.5 gram-atom of magnesium and 83.6 grams of nonylphenol. Results are given in Table 1.

EXAMPLE 14

Example 9 was repeated using a catalyst concentrate containing 6.8 gram-atom of magnesium and 49.3 grams of dinonylphenol. Results are given in Table 1.

EXAMPLE 15

Example 9 was repeated using a catalyst concentrate containing 6.9 gram-atom of magnesium and 3.4 grams of 2,6-di-tert-butyl-p-cresol. Results are given in Table 1.

EXAMPLE 16

An ethoxylation reaction was conducted in a similar manner as in Example 6 except that samples of the product were periodically withdrawn from the reactor and analyzed. Results are given in Table 2.

EXAMPLE 17

A calcium 2-methoxyethoxide catalyst in 2-methoxyethanol solution was prepared by reacting calcium carbide (60 parts, 80% technical grade) with 2-methoxyethanol (900 parts) at reflux condition for 3.5 hours. The catalyst solution containing 3.52% calcium was recovered as a clear liquid after filtration.

To a clean and dried one-gallon kettle was charged EPAL 1214 alcohol (1870 grams) and the above-prepared catalyst solution (108 grams). After stripped off 2-methoxyethanol at 120° and 20 mm Hg, the ethoxylation was conducted at 165° C. and 50 psig. Results are given in Table 3.

EXAMPLE 18

A calcium nonylphenolate catalyst in methanol solution was prepared by reacting calcium carbide, nonylphenol and methanol at reflux for 6 hours. The catalyst solution contained 2.9% calcium and 32% nonylphenol was recovered as clear solution after solids were settled.

To a clean and dried one-gallon kettle was charged EPAL 1214 alcohol (1870 grams) and the above prepared catalyst solution (125 grams). After stripped off methanol at 120° C. and 20 mm Hg, the ethoxylation was conducted at 165° C. and 50 psig. Results are given in Table 3.

EXAMPLE 19

To a clean and dried one-gallon kettle was charged EPAL 1214 alcohol (1870 grams) and strontium hydroxide hexahydrate (25 grams). After stripped of water at 140° C. and 20 mm Hg, the mixture was held at 140° C. for one hour. The ethoxylation was conducted at 165° C. and 80 psig. Results are given in Table 3.

EXAMPLE 20

To a clean and dried one-gallon kettle was charged EPAL 1214 alcohol (1870 grams), strontium hydroxide hexahydrate (25 grams) and nonylphenol (20 grams). After stripped off water, the ethoxylation was conducted at 165° C. and 80 psig. Results are given in Table 3.

EXAMPLE 21

To a clean and dried one-gallon kettle was charged EPAL 1214 alcohol (1870 grams) and barium hydroxide monohydrate (18 grams). After stripped off water, the ethoxylation was conducted at 150° C. and 50 psig. Results are given in Table 3.

EXAMPLE 22

To a clean and dried one-gallon kettle was charged EPAL 1214 alcohol (1870 grams), barium hydroxide monohydrate (18 grams) and nonylphenol (9 grams). After stripped off water, the ethoxylation was conducted at 150° C. and 50 psig. Results are given in Table 3.

TABLE 1

| | ETHOXYLATION OF EPAL 1214 ALCOHOL | | | | | | | | | | | |
|---|---|---|---|---|---|---|---|---|---|---|---|---|
| | EXAMPLES | | | | | | | | | | | |
| | 4 | 5 | 6 | 7 | 8 | 9 | 10 | 11 | 12 | 13 | 14 | 15 |
| CATALYST, Mole % | | | | | | | | | | | | |
| Magnesium Alkoxide | 5.00 | 5.00 | 10.00 | 1.00 | 1.40 | 5.00 | 5.00 | 10.00 | 3.00 | 2.00 | 3.00 | 3.00 |
| Nonylphenol | | | | 1.85 | 0.50 | 2.40 | 2.40 | 4.20 | 3.00 | 4.00 | | |
| Dinonylphenol | | | | | | | | | | | 1.50 | |
| Di-t-butyl-p-cresol | | | | | | | | | | | | 1.50 |
| REACTION CONDITIONS | | | | | | | | | | | | |
| Temperature C | 165 | 150 | 165 | 165 | 165 | 165 | 165 | 165 | 150 | 150 | 165 | 165 |
| Pressure Psig | 80 | 50 | 50 | 80 | 80 | 80 | 80 | 80 | 50 | 50 | 80 | 80 |
| Addition Time Hr | 5.00 | 4.50 | 4.20 | 4.80 | 5.30 | 2.80 | 3.50 | 3.25 | 3.33 | 4.58 | 4.51 | 4.51 |
| PRODUCT | | | | | | | | | | | | |
| # Ave. MW | 496 | 512 | 495 | 495 | 351 | 483 | 498 | 518 | 463 | 493 | 498 | 498 |
| # Mole EO | 6.79 | 7.15 | 6.79 | 6.79 | 3.50 | 6.50 | 6.84 | 7.29 | 6.14 | 6.83 | 6.84 | 6.44 |
| PEG % | 0.75 | 0.27 | 0.50 | 0.70 | 0.74 | 0.56 | 0.56 | 0.41 | 1.24 | 1.03 | 1.24 | 1.25 |
| Peak +/− 2EO Wt % | 66.70 | 64.50 | 66.50 | 64.50 | 70.40 | 70.80 | 67.70 | 65.90 | 68.80 | 66.80 | 66.90 | 67.50 |
| OLIGOMERS | | | | | | | | | | | | |

TABLE 1-continued

ETHOXYLATION OF EPAL 1214 ALCOHOL

| | EXAMPLES | | | | | | | | | | | |
|---|---|---|---|---|---|---|---|---|---|---|---|---|
| | 4 | 5 | 6 | 7 | 8 | 9 | 10 | 11 | 12 | 13 | 14 | 15 |
| 0EO | 0.57 | 0.06 | 0.77 | 1.90 | 4.70 | 0.15 | 0.74 | 0.60 | 0.52 | 0.36 | 0.83 | 0.60 |
| 1EO | 0.62 | 0.41 | 0.36 | 0.77 | 7.79 | 0.48 | 0.10 | 0.14 | 0.73 | 0.46 | 0.17 | 0.30 |
| 2EO | 1.45 | 1.24 | 1.33 | 2.10 | 13.73 | 1.79 | 0.60 | 2.50 | 2.42 | 1.58 | 0.70 | 1.14 |
| 3EO | 3.24 | 3.12 | 3.69 | 3.25 | 16.49 | 4.16 | 1.90 | 5.05 | 5.72 | 3.73 | 2.25 | 3.08 |
| 4EO | 6.11 | 5.88 | 6.42 | 7.27 | 13.57 | 7.95 | 4.36 | 8.32 | 9.97 | 7.04 | 5.30 | 6.45 |
| 5EO | 8.89 | 9.30 | 10.36 | 10.56 | 10.20 | 11.70 | 8.98 | 12.67 | 13.98 | 11.04 | 10.63 | 11.08 |
| 6EO | 11.54 | 12.46 | 13.89 | 13.30 | 7.10 | 15.40 | 14.20 | 14.56 | 16.64 | 14.50 | 14.75 | 14.19 |
| 7EO | 13.57 | 14.74 | 15.79 | 14.76 | 4.41 | 16.62 | 16.93 | 14.77 | 15.38 | 15.17 | 17.33 | 15.32 |
| 8EO | 13.31 | 14.39 | 14.28 | 13.30 | 2.67 | 14.40 | 16.82 | 13.33 | 12.76 | 14.36 | 16.27 | 14.51 |
| 9EO | 12.72 | 12.65 | 12.14 | 9.25 | 1.43 | 12.70 | 14.05 | 10.47 | 9.40 | 11.67 | 12.92 | 12.47 |
| 10EO | 9.22 | 10.85 | 8.77 | 7.13 | 0.67 | 7.61 | 9.82 | 7.20 | 6.04 | 8.50 | 8.77 | 8.89 |
| 11EO | 9.48 | 6.85 | 5.69 | 3.11 | 0.28 | 5.42 | 5.91 | 4.75 | 3.45 | 5.59 | 5.18 | 5.86 |
| 12EO | 4.48 | 4.43 | 3.20 | 1.10 | | 1.41 | 3.16 | 2.68 | 1.75 | 3.11 | 2.69 | 3.20 |
| 13EO | 3.21 | 2.47 | 1.89 | 0.30 | | 0.11 | 1.58 | 1.37 | 0.79 | 1.61 | 1.29 | 1.79 |
| 14EO | 1.51 | 1.28 | 0.92 | | | | 0.45 | 0.50 | 0.31 | 0.75 | 0.64 | 0.76 |
| 15EO | | 0.53 | 0.36 | | | | 0.26 | 0.17 | 0.09 | 0.26 | 0.18 | 0.32 |
| 16EO | | 0.17 | 0.10 | | | | | | | 0.21 | | |
| 17EO | | | | | | | | | | | | |
| 18EO | | | | | | | | | | | | |
| 19EO | | | | | | | | | | | | |
| 20EO | | | | | | | | | | | | |

TABLE 2

ETHOXYLATION OF EPAL 1214 ALCOHOL

| EXAMPLE | | | 16 | | | | | | |
|---|---|---|---|---|---|---|---|---|---|
| SAMPLE NO. | 1 | 2 | 3 | 4 | 5 | | | | |
| CATALYST. Mole % | | | | | | | | | |
| Magnesium Alkoxide | 5.00 | 5.00 | 5.00 | 5.00 | 5.00 | | | | |
| Nonylphenol | 2.30 | 2.30 | 2.30 | 2.30 | 2.30 | | | | |
| REACTION CONDITIONS | | | | | | | | | |
| Temperature °C. | 165 | 165 | 165 | 165 | 165 | | | | |
| Pressure Psig | 80 | 80 | 80 | 80 | 61 | | | | |
| Addition Time Hr | 1.83 | 1.83 | 1.90 | 2.00 | 2.50 | | POISSON DISTRIBUTIONS | | |
| PRODUCT | | | | | | | | | |
| # Ave. MW | 303 | 337 | 377 | 401 | 521 | 303 | 337 | 377 | 401 | 521 |
| # Mole EO | 2.40 | 3.20 | 4.10 | 4.64 | 7.36 | 2.40 | 3.20 | 4.10 | 4.64 | 7.36 |
| PEG % | 0.09 | 0.10 | 0.14 | 0.19 | 0.42 | | | | | |
| Peak +/− 2EO Wt % | 91.00 | 84.50 | 79.35 | 78.00 | 65.20 | 88.43 | 82.34 | 7.44 | 7.07 | 63.72 |
| OLIGOMERS | | | | | | | | | | |
| 0EO | 5.30 | 2.53 | 1.13 | 0.88 | 0.07 | 5.92 | 2.38 | 0.87 | 0.48 | 0.02 |
| 1EO | 14.29 | 7.58 | 3.64 | 2.32 | 0.27 | 17.36 | 9.32 | 4.35 | 2.70 | 0.22 |
| 2EO | 27.23 | 18.48 | 9.94 | 7.40 | 0.87 | 24.61 | 17.62 | 10.53 | 7.39 | 0.94 |
| 3EO | 26.02 | 23.31 | 17.16 | 12.85 | 2.45 | 22.72 | 21.68 | 16.60 | 13.19 | 2.67 |
| 4EO | 16.12 | 20.78 | 19.99 | 16.96 | 4.87 | 15.45 | 19.66 | 19.29 | 17.35 | 5.58 |
| 5EO | 7.47 | 14.28 | 18.57 | 18.16 | 8.28 | 8.29 | 14.06 | 17.67 | 17.99 | 9.17 |
| 6EO | 2.59 | 7.66 | 13.68 | 15.89 | 11.61 | 3.66 | 8.29 | 13.35 | 15.38 | 12.43 |
| 7EO | 0.88 | 3.41 | 8.60 | 12.13 | 14.32 | 1.38 | 4.15 | 8.56 | 11.16 | 14.32 |
| 8EO | | 1.32 | 4.23 | 6.79 | 14.74 | 0.45 | 1.80 | 4.77 | 7.04 | 14.32 |
| 9EO | | 0.42 | 1.90 | 3.64 | 13.32 | 0.13 | 0.69 | 2.35 | 3.92 | 12.65 |
| 10EO | | 0.17 | 0.72 | 1.65 | 10.91 | 0.03 | 0.24 | 1.03 | 3.92 | 10.00 |
| 11EO | | 0.04 | 0.21 | 0.71 | 7.70 | 0.01 | 0.07 | 0.41 | 1.95 | 7.15 |
| 12EO | | | 0.06 | 0.34 | 5.16 | | 0.02 | 0.15 | 0.88 | 4.67 |
| 13EO | | | 0.04 | 0.15 | 2.94 | | 0.01 | 0.05 | 0.36 | 2.80 |
| 14EO | | | | 0.06 | 1.57 | | | 0.02 | 0.14 | 1.56 |
| 15EO | | | | | 0.65 | | | | 0.05 | 0.81 |
| 16EO | | | | | 0.23 | | | | 0.02 | 0.39 |
| 17EO | | | | | | | | | | 0.18 |
| 18EO | | | | | | | | | | 0.08 |
| 19EO | | | | | | | | | | 0.03 |
| 20EO | | | | | | | | | | 0.01 |

TABLE 3

| | | | Comparative Examples | | | | | |
|---|---|---|---|---|---|---|---|---|
| EXAMPLE NO. | 8 | 13 | 17 | 18 | 19 | 20 | 21 | 22 |
| CATALYST, Mole % | | | | | | | | |
| Magnesium Alkoxide | 1.00 | 2.00 | | | | | | |
| Calcium Alkoxide | | | 1.00 | 2.90 | | | | |
| Strontium Alkoxide | | | | | 1.00 | 1.00 | | |
| Barium Alkoxide | | | | | | | 1.00 | 1.00 |
| Nonylphenol | 1.85 | 4.00 | 2.00 | | 2.00 | | 2.00 | |
| REACTION CONDITIONS | | | | | | | | |

TABLE 3-continued

| | Comparative Examples | | | | | | | | | |
|---|---|---|---|---|---|---|---|---|---|---|
| EXAMPLE NO. | 8 | 13 | 17 | 18 | 19 | 20 | 21 | 22 | | |
| Temperature °C. | 165 | 150 | 165 | 140 | 165 | 165 | 150 | 150 | | |
| Pressure Psig | 80 | 50 | 80 | 50 | 80 | 80 | 50 | 50 | | |
| Addition Time Hr | 4.80 | 4.58 | 2.00 | 3.00 | 2.35 | 1.00 | 1.60 | 1.15 | | |
| PRODUCT | | | | | | | | | POISSON DISTRIBUTION | |
| # Ave. MW | 495 | 493 | 493 | 502 | 515.00 | 490 | 523 | 511 | | |
| # Mole EO | 6.79 | 68.30 | 6.79 | 6.93 | 7.23 | 6.66 | 7.40 | 7.13 | 7.00 | 7.40 |
| PEG % | 0.70 | 1.03 | 0.22 | 3.50 | 1.23 | 1.50 | 3.11 | 2.02 | | |
| Peak +/− 2EO Wt % | 61.17 | 66.80 | 64.70 | 66.34 | 6.18 | 64.40 | 62.90 | 61.93 | 65.20 | 63.69 |
| OLIGOMERS | | | | | | | | | | |
| 0EO | 1.90 | 0.36 | 1.17 | 0.12 | 1.21 | 0.96 | 0.50 | 0.59 | 0.03 | 0.02 |
| 1EO | 0.77 | 0.46 | 0.63 | 0.50 | 0.36 | 0.76 | 0.57 | 0.70 | 0.30 | 0.21 |
| 2EO | 2.10 | 1.58 | 1.71 | 1.63 | 0.70 | 1.97 | 1.19 | 1.48 | 0.13 | 0.91 |
| 3EO | 3.25 | 3.73 | 3.37 | 3.27 | 2.57 | 3.97 | 2.66 | 3.25 | 3.40 | 2.60 |
| 4EO | 7.27 | 7.04 | 6.23 | 6.06 | 5.69 | 6.39 | 4.78 | 5.69 | 6.70 | 5.46 |
| 5EO | 10.56 | 11.04 | 9.73 | 10.36 | 8.52 | 9.27 | 7.41 | 8.39 | 10.60 | 9.02 |
| 6EO | 13.30 | 14.50 | 12.73 | 13.51 | 11.55 | 15.50 | 11.00 | 11.70 | 13.60 | 12.30 |
| 7EO | 14.76 | 15.17 | 14.93 | 15.10 | 13.29 | 13.67 | 13.45 | 13.55 | 14.90 | 14.24 |
| 8EO | 13.30 | 14.36 | 12.62 | 14.72 | 13.73 | 13.56 | 14.24 | 13.91 | 14.20 | 14.32 |
| 9EO | 9.25 | 11.67 | 9.93 | 12.65 | 12.70 | 11.62 | 13.22 | 12.62 | 11.90 | 12.72 |
| 10EO | 7.13 | 8.50 | 6.25 | 9.45 | 10.38 | 8.79 | 11.00 | 10.15 | 8.90 | 10.11 |
| 11EO | 3.11 | 5.59 | 4.02 | 5.83 | 7.77 | 5.94 | 8.23 | 7.40 | 6.10 | 7.27 |
| 12EO | 1.10 | 3.11 | 1.53 | 3.55 | 5.32 | 3.63 | 5.46 | 4.88 | 3.80 | 4.77 |
| 13EO | 0.30 | 1.61 | 0.35 | 1.82 | 3.18 | 2.13 | 3.37 | 2.84 | 2.20 | 2.88 |
| 14EO | | 0.75 | 0.19 | 0.64 | 1.73 | 1.12 | 1.74 | 1.56 | 1.10 | 1.61 |
| 15EO | | 0.26 | 0.07 | 0.34 | 0.78 | 0.68 | 0.82 | 0.75 | 0.30 | 0.84 |
| 16EO | | 0.21 | | 0.24 | 0.38 | | 0.32 | 0.35 | 0.10 | 0.41 |
| 17EO | | | | | | | | 0.15 | | 0.19 |
| 18EO | | | | | | | | | | 0.08 |
| 19EO | | | | | | | | | | 0.03 |
| 20EO | | | | | | | | | | 0.01 |

We claim:

1. A method for the alkoxylation of a reactive hydrogen compound selected from the group consisting of monohydric alcohol(s) having between about 6 and about 30 carbon atoms, both branched and linear, with an alkylene oxide having two to four carbon atoms comprising reacting said monohydric alcohol(s) with said alkylene oxide at a temperature at which the reaction proceeds in the presence of at least a catalytic amount of a material consisting of a catalyst that is produced by the reaction of magnesium and a phenolic compound wherein the alkoxylation product has a narrow molecular weight distribution.

2. A method as in claim 1 wherein the phenolic compound is nonylphenol.

3. A method for the alkoxyalation of a reactive hydrogen compound selected from the group consisting of monohydric alcohols having between about 6 and about 30 carbon atoms, both branched and linear, with an alkylene oxide having two to four carbon atoms comprising reacting said monohydric alcohol(s) with said alkylene oxide at a temperature at which the reaction proceeds in the presence of at least a catalytic amount of a material consisting of a catalyst that is produced by reacting a phenolic compound with magnesium alkoxide from the reaction of magnesium and a mixture of high molecular weight alcohol(s) and low molecular weight alcohol(s) and the subsequent removal of the low molecular weight alcohol(s), wherein the alkoxylation product has a narrow molecular weight distribution.

4. A method as in claim 3 wherein the phenolic compound is nonylphenol.

* * * * *